( 12 ) United States Patent
Huang et al.

(10) Patent No.: US 8,776,791 B2
(45) Date of Patent: Jul. 15, 2014

(54) RESPIRATOR AND METHOD FOR CALIBRATING FLOW RATE MEASURING COMPONENT THEREOF

(75) Inventors: Lintao Huang, Shenzhen (CN); Xinsheng Li, Shenzhen (CN); Ruiling Pan, Shenzhen (CN); Xiaoyong Zhou, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1715 days.

(21) Appl. No.: 11/951,479

(22) Filed: Dec. 6, 2007

(65) Prior Publication Data

US 2008/0257350 A1 Oct. 23, 2008

(30) Foreign Application Priority Data

Apr. 18, 2007 (CN) .......................... 2007 1 0074072

(51) Int. Cl.
*A61M 16/00* (2006.01)
*A62B 9/02* (2006.01)

(52) U.S. Cl.
USPC ............. 128/204.21; 128/204.18; 128/205.24

(58) Field of Classification Search
CPC ............ A61M 16/00; A61M 16/0051; A61M 16/0057; A61M 16/0075; A61M 16/08; A61M 16/10; A61M 16/20–16/208; A61M 2016/00; A61M 2016/003; A61M 2016/0027–2016/0057; A61M 2016/0081; A61M 2016/08; A61M 2016/208; A62B 7/00–7/04; A62B 9/00; A62B 9/02; A62B 27/00
USPC ............. 128/204.18, 204.21–204.23, 204.26, 128/204.28, 205.11, 205.13–205.18, 5.24
See application file for complete search history.

(56) References Cited

U.S. PATENT DOCUMENTS 4,224,940 A * 9/1980 Monnier .................. 128/205.16
5,315,989 A * 5/1994 Tobia ....................... 128/204.28
(Continued)

FOREIGN PATENT DOCUMENTS

| CN | 2154707 | 2/1994 |
| CN | 1094969 | 11/1994 |
| CN | 2907722 | 6/2007 |
| JP | 2007272848 | 9/2002 |

OTHER PUBLICATIONS

Chinese Search Report dated Aug. 8, 2007 for Chinese Patent Application 200710074072.0.
(Continued)

*Primary Examiner* — Justine Yu
*Assistant Examiner* — Rachel Young
(74) *Attorney, Agent, or Firm* — Kory D. Christensen; Stoel Rives LLP

(57) ABSTRACT

A respiration apparatus and a method for calibrating respiration parameters thereof are provided. A flow measuring reference component arranged behind the inspiratory valve in the ventilator is used as a flow measuring reference sensor for calibrating the flow sensor so that the flow rates of the gas through the flow measuring reference component and the flow sensor to be calibrated are identical or in a corresponding relation. Electrical parameters output from the flow sensor and the flow measuring reference component are respectively acquired and processed to obtain a relation curve of the gas flow rate and the electrical parameter of the flow sensor on the basis of the read gas flow rate and the electrical parameters of the flow sensor. The present invention enables automatic calibration for a flow sensor without using any measuring instrument.

17 Claims, 5 Drawing Sheets

(56) References Cited

U.S. PATENT DOCUMENTS

| | | | |
|---|---|---|---|
| 5,490,499 A * | 2/1996 | Heinonen et al. | 128/203.28 |
| 5,509,406 A * | 4/1996 | Kock et al. | 128/203.14 |
| 5,706,801 A * | 1/1998 | Remes et al. | 128/202.26 |
| 6,599,253 B1 | 7/2003 | Baum et al. | |
| 6,776,158 B1 | 8/2004 | Anderson et al. | |
| 7,195,594 B2 * | 3/2007 | Eigler et al. | 600/485 |
| 2003/0106554 A1 * | 6/2003 | de Silva et al. | 128/204.22 |
| 2008/0011298 A1 * | 1/2008 | Mazar et al. | 128/204.18 |

OTHER PUBLICATIONS

English translation of abstract for Japanese Patent No. 2002272848, Chinese Patent No. 2154707, Chinese Patent No. 2907722 and Chinese Patent No. 1094969.

* cited by examiner

RESPIRATOR AND METHOD FOR CALIBRATING FLOW RATE MEASURING COMPONENT THEREOF

TECHNICAL FIELD

The present invention relates to a respirator for assisting a patient's breathing, and more particularly, to a respirator that calibrates a flow sensor for monitoring respiration mechanics parameters therein and a method for calibrating a flow sensor thereof.

DESCRIPTION OF PRIOR ART

A respirator, also known as a ventilator, is a facility to implement mechanical ventilation for assisting and controlling a patient's breathing, improving his or her oxygenation and ventilation, reducing work by respiratory muscles, supporting circulatory functions and also for treating a respiratory failure. Respirator apparatus for assisting a patient's breathing, such as anesthetic machines are often used in medical treatment depending on a patient's medical condition. An anesthetic machine functions to provide inhalation anesthesia and mechanical ventilation for a patient during an operation. Since an effective implementation of mechanical ventilation necessitates an accurate monitoring of various respiration mechanics parameters, respiration mechanics parameters associated with ventilation safety such as tidal volume, respiratory rate, exhaled minute volume and respiration flow rate need to be monitored while providing mechanical ventilation for a patient, which are measured by a flow sensor capable of measuring gas flow rate. Also, the implementation of various ventilation modes depends on the accurate measurement of the flow sensor. Therefore the reliability and accuracy of a flow sensor determines the performance of a respirator directly.

However, during the operation of a respirator, a measured value and an actual value often differ greatly due to sensor aging, damage, temperature drift, water accumulation or individual variation among sensors of the same type, which are common in practical application. When a large deviation occurs in the measurements of a flow sensor, generally the flow sensor needs to be recalibrated in order to ensure the accuracy and safety of ventilation control.

A calibration for a flow sensor is to establish a corresponding relationship between the flow rate and the output voltage of the flow sensor. Particularly, within the operating range of flow rate conditions for a respirator system, a plurality of constant gas streams with known flow rates are applied to the flow sensor; for each of the known flow rates, a output voltage at the flow sensor is detected; and the relationship between the gas flow rates and the output voltages are stored in a nonvolatile memory so as to accomplish a calibrating process for the flow sensor.

For an anesthesia respirator actuated and controlled electrically, constant gas streams with set flow rate may be provided by accurately controlling the piston to scale the flow sensor. However, for a commonly used anesthetic respirator actuated pneumatically and controlled electrically, it's impossible to ensure that the actual stream flow velocity coincides with the set value by controlling valves. It is therefore necessary to use additional flow velocity measuring devices to obtain the actual gas flow rate.

According to the above flow sensor scaling principle, generally a flow velocity detecting instrument is provided to measure the accurate gas velocity. Therefore, currently common calibrating methods for the anesthesia machines actuated pneumatically and controlled electrically are manual calibration or automatic calibration with flow velocity detecting instruments.

1) Manual calibration: The gas outlet of a respirator is connected to a flow rate detecting instrument such that gas streams flowing through the detecting instrument and the flow sensor have identical velocities. The inspiratory flow rate through the flow sensor is changed by closing the exhalation valve and manually regulating the open degree of the inspiratory valve, and when the reading of the flow velocity detecting instrument is stabilized at the preset flow velocity value, the microprocessor is made by manual confirmation to record current output voltage values of the flow sensor.

2) Automatic calibration: Also, a measuring instrument and a flow sensor is connected in series at the gas outlet of a respirator such that gas streams through both of them are identical. The exhalation valve is closed and the software automatically opens the inspiratory valve gradually. After each open degree is set and the gas stream gets stabilized, a flow rate value of the measuring instrument is read through serial port communication and a current output voltage of sensor is recorded.

In summary, a shortcoming in the calibration for the flow sensor of a prior art respirator actuated pneumatically and controlled electrically is that an additional measuring instrument is required for either manual or automatic calibration. Since a user generally does not have any flow velocity detecting instruments matching calibration requirements, the maintenance and calibration can only be provided by the factory, which greatly limits the convenience, safety and reliability of the use of respirators.

SUMMARY OF THE INVENTION

Therefore, an object of the present invention is to solve the above-mentioned problems in the prior art by providing a new-type respirator and a method for calibrating respiration parameters thereof that enables a user to calibrate the flow sensor conveniently as required, hence ensuring the safety and reliability of the respirator.

To achieve the above object, the present invention provides a respirator comprising:

an inspiratory valve for allowing driving gas from external gas supply to enter;

a bellows provided with a gasbag therein to which a pressure may be applied by the driving gas entering the bellows so as to compress fresh gases in the bag to be discharged;

a check valve for letting the discharged fresh gas flow toward a patient; and a flow measuring component for detecting a flow rate of said fresh gas flowing through the check valve to provide respiration parameters of the patient, wherein a flow measuring reference component is provided between the inspiratory valve and the check valve, and the provided respiratory parameters are calibrated on the basis of the corresponding relation between the flow rate of the gas through the flow measuring reference component and the flow rate of the gas through the flow measuring component.

In addition, the present invention provides a method for calibrating a flow measuring component in the above mentioned respirator, comprising the steps of:

detecting a gas flowing through the flow measuring reference component to obtain basic parameters associated with a flow rate of the gas;

detecting a gas flowing through the flow measuring component to obtain measured parameters associated with a flow rate of the gas;

obtaining the flow rates of the gas through the flow measuring reference component on the basis of the basic parameters;

obtaining the flow rates of the gas corresponding to the measured parameters on the basis of a corresponding relation between the flow rates of the gas through the flow measuring reference component and the flow rates of the gas through the flow measuring component, to provide the respiration parameters based on the gas flow rates corresponding to the measured parameters.

The features and advantages of the present invention will be described in detail hereinafter with reference to embodiments thereof in conjunction with the accompanying drawings.

DETAIL DESCRIPTION OF THE INVENTION

The fundamental operating principle of a medically common used respirator is as follows. The majority of commonly used respirators operate with an interior and an exterior circuit of a gasbag or foldable bellows. The interior ring airway and gas stream communicate with the patient's air passage while the exterior ring airway and gas stream is used to compress the breather bags or bellows to press fresh gas, which is also known as driving gas, in the bags or bellows into the alveoli of the patient for gas exchange. Due to the exterior ring airway is not communicated with the air passage of the patient, compressed oxygen or compressed air is generally used as the driving gas.

In clinical applications, it is required that the respirator, while providing mechanical ventilation for a patient, is also capable of providing various respiration mechanics parameters of the patient including tidal volume, respiratory rate, exhaled minute volume and respiratory flow rate, which are measured by a flow sensor for measuring gas flow rate. A typical measurement process comprises: detecting the gas velocity and outputting a relevant electrical parameter such as a voltage by a flow measuring component near the patient; sampling the electrical parameter by signal sampling and processing circuit, and outputting signal after amplification and analog-to-digital conversion to a microprocessor; calculating a flow rate corresponding to the electrical parameter by the microprocessor based on the relationship between the gas velocities of the flow measuring component and the electrical parameters read from a memory; and calculating various respiration mechanics parameters based on the gas flow rate.

During the operation of a respirator, a measured value and an actual value often differ greatly due to sensor aging, damage, temperature drift, water accumulation or individual variation among sensors of identical type, which are common in practical application. When a large deviation occurs in the measurements of a flow sensor, generally the flow sensor needs to be recalibrated in order to ensure the accuracy and safety of ventilation control.

The gist of this invention lies in that, by providing as a reference a flow measuring reference component in the gas passage between the inspiratory valve and the check valve of a respirator, the gas flow rates corresponding to measured parameters of the flow measuring component is obtained on the basis of a corresponding relationship between the flow rate of the gas through the flow measuring reference component and that of the gas through the flow measuring component to provide respiration parameters based on flow rates corresponding to the measured parameters.

First Embodiment

Figure 1:
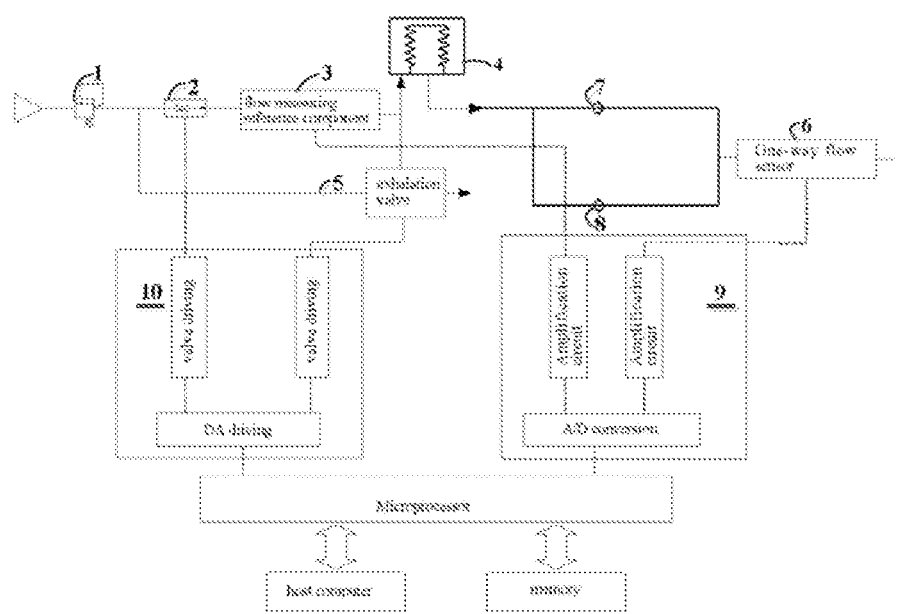
FIG. 1 is a structural principle diagram of the respirator according to the first embodiment of the present invention.

As shown in FIG. 1, a respirator according to the present invention comprises a pressure regulator 1, an inspiratory valve 2, an exhalation valve 5, a flow sensor 6, a flow measuring reference component 3, bellows 4, an inspiratory check valve 7, an expiratory check valve 8, a signal sampling and processing circuit 9 and a control circuit 10.

The inspiratory valve 2 can cause driving gas from external gas supply to be sucked in response to a control signal of the control circuit 10.

The bellows 4 is provided with a gasbag therein to which a pressure may be applied by the driving gas sucked into the bellows so as to compress fresh gases in the bag to be discharged.

The inspiratory check valve 7 operates to let the discharged fresh gas flow forward the patient.

The flow sensor 6 adopted in this embodiment is a one-way flow sensor that detects the flow rate of fresh gas flowing from the inspiratory check valve to the patient, to provide respiration parameters of the patient.

In this respirator, a flow measuring reference component 3 is provided between the inspiratory valve 2 and the bellows 4, through which the driving gas entering from the inspiratory valve 2 flows into the bellows.

In clinical use of the respirator, the bag in the bellows 4 is filled with fresh gas of oxygen and anesthetic gas. When the patient inhales, the microcontroller outputs a control signal to the control circuit 10 to let it generate a control signal to open the inspiratory valve 2 and close the exhalation valve 5. The driving gas generated from a high-pressure tank or a central gas supply system reaches the bellows 4 via the pressure regulator 1, the inspiratory valve 2 and the flow measuring reference component 3 and enters into the space outside of the bag in the bellows 4. As the driving gas increases, the bag is compressed to force fresh gas in the bag pass the inspiratory check valve 7 and finally be provided to the patient through the flow measuring component.

When the patient exhales, the control circuit 10 generates a control signal to close the inspiratory valve 2 and open the exhalation valve 5. Gas streams exhaled by the patient enter the gasbag from a connection device at the patient via the expiratory check valve 8. The gasbag expands due to gas filling and forces the gas in the space outside of the bag in bellows 4 to be discharged through the exhalation valve 5.

Figure 2:
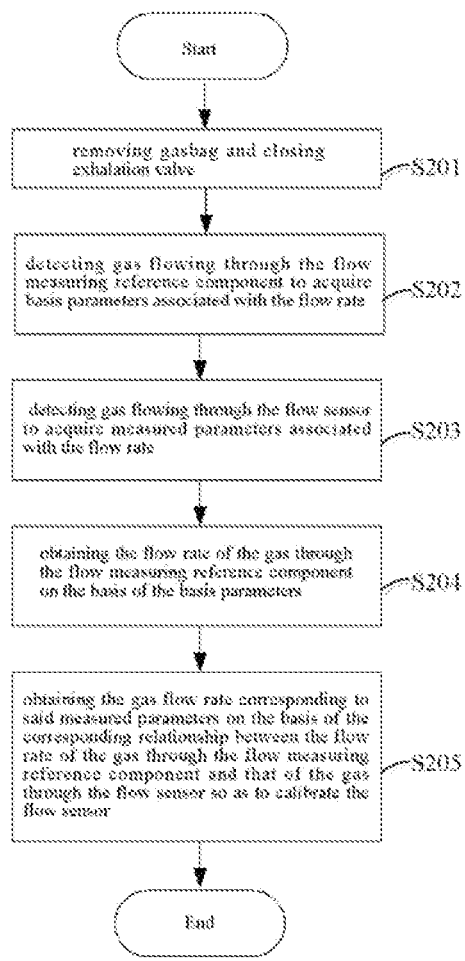
FIG. 2 is a calibration flow chart for a flow measuring component of the respirator according to the first embodiment of the present invention.

The calibration process for the flow measuring component of the respirator according to the first embodiment of the present invention will be described in detail with reference to FIGS. 1 and 2.

To calibrate the flow sensor 6 arranged near the patient, first the gasbag in the bellows 4 is removed and the exhalation valve 5 is closed (Step S201). In this case, the driving gas is discharged to the atmosphere through the inspiratory valve 2, the flow measuring reference component 3, the bellows 4 and the flow sensor 6.

Next, the gas flowing through the flow measuring reference component 3 is detected to acquire basic parameters associated with the gas flow rate, such as the output voltage value (Step S202).

Then, the gas flowing through the flow sensor is detected to acquire the measured parameters associated with the gas flow rate, such as the output voltage value (Step S203).

The flow rate of the gas through the flow measuring reference component 3 is obtained according to the basic parameters (Step S204).

Finally, the gas flow rate corresponding to said measured parameters is obtained on the basis of the corresponding relationship between the flow rate of the gas through the flow measuring reference component and that of the gas through the flow sensor (in this embodiment, since there is no fresh gas, the gas flow rate measured by the flow measuring reference component 3 is equal to that through the flow sensor 6), so as to provide the respiration parameters based on the flow rate corresponding to said measured parameters (Step S205).

The microprocessor may control different open degrees of the inspiratory valve 2 by the control circuit 10 to change the gas flow rate through the flow measuring reference component and the flow sensor. Actual output electrical parameters from the flow sensor under various flow rates may be obtained by repeating the above steps S202 to S205, which enables calibration of the measured respiration parameters of the flow sensor after a period of use.

In the present embodiment, since the flow measuring reference component 3 is provided between the inspiratory valve 2 and the bellows 4, dry driving gas flows through the flow measuring reference component and thereby the flow measuring reference component is not influenced by the condensed water and secretions in the patient's circuit, which ensures the stability, reliability and lifespan of the flow measuring reference component.

In addition, the flow sensor needs not be reversed for measurement since the flow sensor in this embodiment is a one-way flow sensor.

In this embodiment, removing the gasbag in the bellows 4 and closing the exhalation valve 5 make the gas flow rate measured by the flow measuring reference component 3 equals to that through the flow sensor 6. However the present invention is not limited thereto. It is noted that, one can also conceive to obtain the respiration parameters based on the gas flow rates corresponding to the measured parameters on the basis of the proportional relation (corresponding relation) between the gas flow rate (of the driving gas) through the flow measuring reference component 3 and the gas flow rate (of the fresh gas) through the flow sensor 6 without removing the gasbag in the bellows 4.

Second Embodiment

Figure 3:
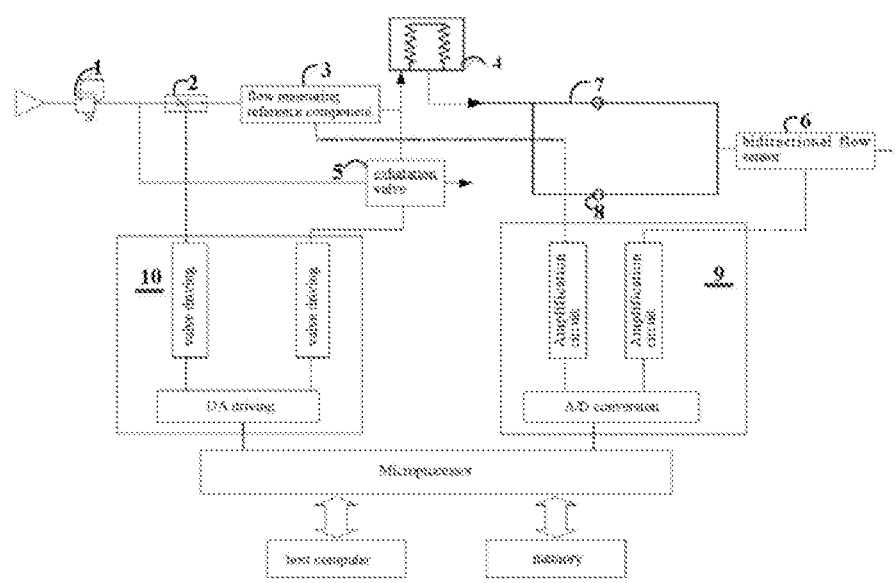
FIG. 3 is a structural principle diagram of the respirator according to the second embodiment of the present invention.

As shown in FIG. 3, the present embodiment has substantially the same configuration as that of the first embodiment of the present invention except that the flow sensor 6 is a bidirectional flow sensor. Therefore components identical or similar to those of the first embodiment will not be described again.

Since the flow sensor 6 is a bidirectional flow sensor, it can detect gas flow rates of both inhalation and exhalation of the patient.

When the flow sensor 6 is a bidirectional flow sensor, it is arranged near the patient as shown in FIG. 3. A bidirectional flow sensor can measure the gas flow rate flowing into any one of the two ports thereof, however rate measurements in the two directions, that is, the directions of flowing into one port and the other, have certain difference and a doctor may place the bidirectional flow sensor randomly in use. Therefore, as compared with a one-way flow sensor, a relation between measurements, such as output voltages, and the flow rates in two directions of the bidirectional flow sensor needs to be obtained so that the doctor can obtain relevant respiration parameters with a flow rate versus output voltage relation corresponding to the direction selected during clinical use.

Figure 4:
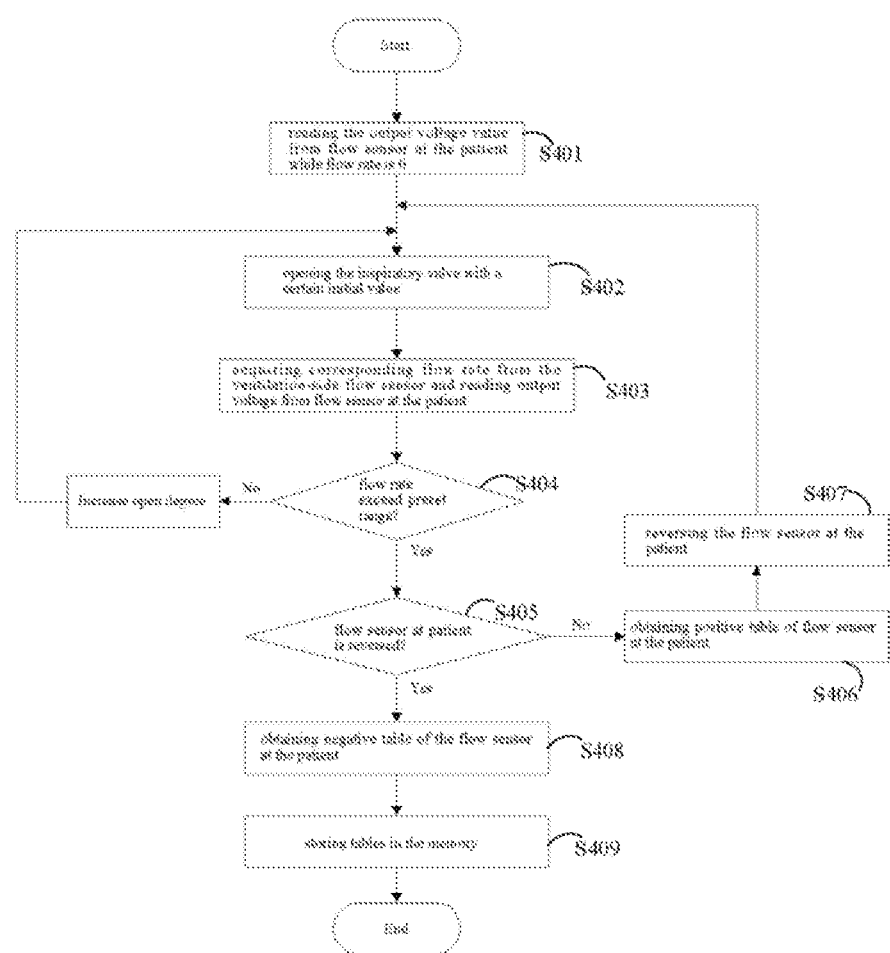
FIG. 4 is a calibration flow chart for a flow measuring component of the respirator according to the second embodiment of the present invention.

The calibration procedure for the flow measuring component of the respirator according to the second embodiment of the present invention will be described hereinafter with the bidirectional flow sensor as an example. Referring to FIG. 4, it comprises the following steps:

First, with both the inspiratory valve and the exhalation valve closed and hence no gas stream flowing through the flow sensor 6, the voltage values measured by the sampling and amplifying circuit now correspond to the output voltages of the flow sensor 6 at the patient when the flow rate is zero (Step S401).

Next, the inspiratory valve 2 is opened to a certain degree by the control circuit 10 (Step S402).

Then, output voltages of the flow sensor 6 to be calibrated and the flow measuring reference component 3 as a reference are read, and the gas flow rate through the flow measuring reference component 3 at this time is obtained on the basis of the known rate-voltage relation curve of the flow measuring reference component. Since in this case the gas flow rate through the flow sensor 6 should be equal to that through the flow measuring reference component, the rate through the flow sensor 6 is accordingly obtained after that through the flow measuring reference component 3 is obtained (Step S403).

Thereafter, determining whether the gas flow rates go beyond a preset range (Step S404), and if not (No at Step S404), the microprocessor increases the open degree of the inspiratory valve little by little. Each time a certain open degree is set and the gas stream get stabilized, the flow rate values measured by the flow measuring reference component 3 and the voltage values output by the flow sensor 6 are read (repeating Steps S402 to S403).

When the measured gas flow rates go beyond the preset range (i.e. reaching the measurement upper limit) (Yes at Step S404), the microprocessor determines whether the flow sensor 6 is reversed (Step S405), and if not (No at Step S405), it is possible to obtain a positive relation table of the gas flow rate and the voltage of the flow sensor 6, which is a table of rate-voltage relation measured by the forward installed bidirectional flow sensor 6, on the basis of a series of measured gas flow rates and the output voltage values of the flow sensor 6.

After the above operations are completed, the microprocessor prompts the user to reverse the flow sensor 6 through a host computer (Step S407). After receiving confirmation commands for a user to reverse the flow sensor sent from the host computer, the above operation steps S402 to S404 are repeated to obtain a negative relation table of the gas flow rates and the voltages of the flow sensor 6, which is a table of relation between gas flow rates and voltages measured by a backward installed bidirectional flow sensor 6 (Step S408).

Finally, the microprocessor stores the corresponding relations between the rates and output voltages measured in both directions by the bidirectional flow sensor 6 in a memory (Step S409) so as to complete the calibration process for the flow sensor 6.

During use, the microprocessor detects the flow direction of the fresh gas through the bidirectional flow sensor, that is, from which of the two ports of the bidirectional flow sensor the fresh gas flows. Next, respiration mechanics parameters of the patient are also obtained on the basis of the detected flow direction and the measurement results of the flow measuring component 6.

It is noted that, the newly added flow measuring reference component 3 not only functions to calibrate the flow sensor 6 at the patient but also to determine whether the sensor 6 at the patient malfunctions and generate an alarm signal in case of any failure. Furthermore, the newly added flow measuring reference component is used as a reference to control the inspiratory valve so as to ensure the safety of ventilation.

Third Embodiment

Figure 5:
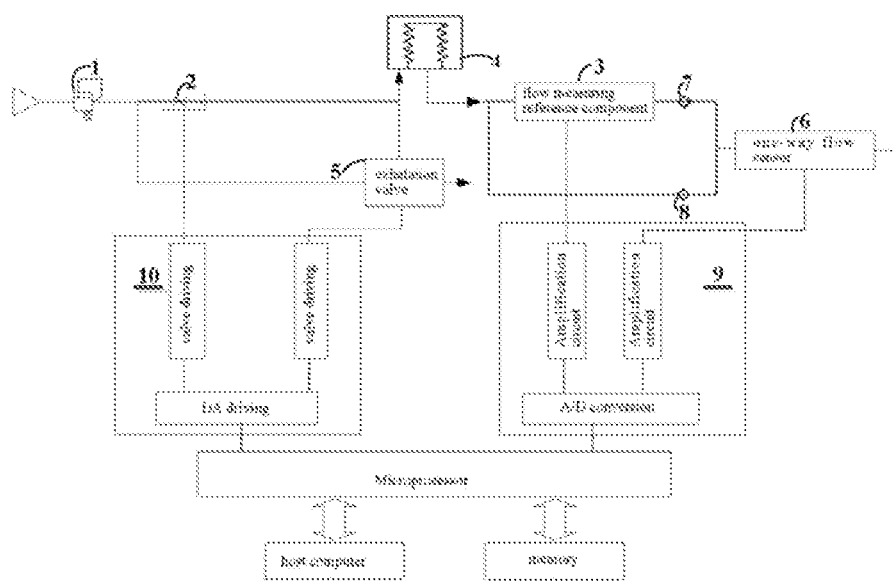
FIG. 5 is a structural principle diagram of the respirator according to the third embodiment of the present invention.

As shown in FIG. 5, the respirator of the present embodiment has substantially the same configuration as that of the first embodiment of the present invention except that the flow measuring reference component 3 is provided between the bellows 4 and the inspiratory check valve 7. Therefore, the calibration process for the flow sensor 6 of the present embodiment is the same as that of the first embodiment. Components that are identical or similar to those of the first embodiment will not be described again.

Modifications of the Invention

In the embodiments of the present invention, a flow sensor is used as the flow measuring component, however the present invention is not limited thereto. Any flow sensors that are capable of measuring gas flow rate, including common pressure type flow sensors and hot filament flow sensors, can be used for the above mentioned flow measuring component and the flow measuring reference component, in which a differential pressure type flow sensor may be used as the pressure type flow sensor.

To further improve the stability of the flow measuring reference component, a differential pressure sensor of fixed aperture may be used as the flow measuring reference component. Since the sensitivity of the differential pressure sensor with fixed aperture is lower than that of a differential pressure sensor with variable aperture, it is preferred that a differential pressure sensor with variable aperture is also used for the flow measuring component to sense minute gas stream.

Beneficial Effects

The present invention improves the deficiency of prior art calibration technique, enables the user to calibrate the flow measuring component timely as required and improves the accuracy of the flow measuring component, hence ensuring the safety and reliability of the respirator by providing a stable and reliable flow measuring reference component for calibrating the flow measuring component in the airway between the inspiratory valve and the inspiratory check valve of the respiration apparatus in place of the measuring instrument.

In addition, since the flow measuring reference component as a reference is provided between the inspiratory valve and the bellows, dry driving gas is flowing therethrough and it will not be influenced by the condensed vapors and secretions in the patient circuit, resulting in a more stable measurements, a longer lifespan and a lower swapping frequency.

Thirdly, the stability of the flow measuring reference component may be further guaranteed if a differential pressure sensor with fixed aperture is used for the flow measuring reference component as a reference.

To sum up, the present invention enables automatic calibration for a flow sensor without the need of using any measuring instrument, which ensures the accuracy and reliability of the measured data and also allows operations at any moment and any place, greatly facilitating the use by a user.

It is understood by those skilled in the art that various modifications are possible in the above anesthesia machine respiration apparatus and calibrating method for the flow sensor as disclosed in the present invention without departing from the scope of the present invention. Therefore the protection scope of the present invention should be defined by the appended claims.

While the present invention has been described with reference to preferred embodiments, it is not intended to be limited to the specific forms described herein. Further, the scope of the present invention is only limited by the appended claims. In the claims, terms "comprise" or "comprising" do not exclude the presence of other elements or steps. In addition, a plurality of devices, elements or steps of a method may be embodied in, for example, one single unit or processor although they are set forth separately. In addition, while individual features may be included in different claims, these features may be combined advantageously and the inclusion in different claims does not imply that the combinations of features are impossible and/or disadvantageous.

The invention claimed is:

1. A respirator, comprising:
   an inspiratory valve to deliver driving gas from an external gas supply source to drive one or more gases to a patient during a medical treatment procedure;
   a bellows including a container therein to which a pressure is applied by the driving gas, which enters the bellows to compress the one or more gases in the container in order to discharge the one or more gases through a breathing circuit between the container and a discharge end to the patient who is undergoing the medical treatment procedure;
   a flow measuring component that is situated near the discharge end near the patient in the breathing circuit to detect a first flow rate of the one or more gases provided for inhalation or an exhaled gas flow rate of an exhaled gas from the patient and to provide one or more respiration parameters of the patient;
   a flow measuring reference component that is provided between the inspiratory valve and the container to detect a second flow rate of the driving gas, wherein
      the flow measuring reference component sends a first signal in response to at least one of the one or more respiration parameters measured by the flow measuring component to a processing circuit that issues a second signal to cause a control circuit to issue one or more control signals comprise a control signal to calibrate and adjust an opening of the inspiratory valve during the medical treatment procedure based at least in part upon the second flow rate of the driving gas and the first flow rate of the one or more gases and a warning signal to indicate that the flow measuring component is not functioning correctly when the flow measuring component malfunctions.

2. The respirator according to claim 1, wherein the flow measuring component comprises a first flow sensor to detect the first flow rate and the flow measuring reference component comprises a second flow sensor to detect the second flow rate.

3. The respirator according to claim 2, wherein the first flow sensor or the second flow sensor comprises a pressure type flow sensor or a hot filament flow sensor.

4. The respirator according to claim 3, wherein the pressure type flow sensor comprises a differential pressure type flow sensor.

5. The respirator according to claim 4, wherein the differential pressure type flow sensor comprises a fixed aperture or a variable aperture.

6. The respirator according to claim 5, wherein the flow measuring component comprises the variable aperture, and the flow measuring reference component comprises fixed aperture.

7. The respirator according to claim 2, wherein the flow measuring component comprises a bidirectional flow sensor.

8. The respirator according to claim 7, wherein the bidirectional flow sensor comprises two ports and the one or more gases flow through at least one of the two ports, and a corresponding relation depends on a respective port through which the one or more gases flow into the bidirectional flow sensor.

9. A method for calibrating a flow measuring component of a respirator, comprising:
obtaining one or more basic parameters that are associated with a first flow rate of a driving gas that flows through a flow measuring reference component;
determining one or more measured parameters that are associated with a second flow rate of one or more gases that flow through the flow measuring component, wherein
the one or more gases are to be discharged to a patient during a medical treatment procedure by using the driving gas to compress a container that is used to accommodate the one or more gases;
determining the second flow rate corresponding to the one or more measured parameters based at least in part upon a third flow rate of the driving gas through the flow measuring reference component that is determined based at least in part upon the one or more basic parameters;
determining the one or more respiration parameters based at least in part on the second gas flow rate corresponding to the one or more measured parameters; and
using the flow measuring reference component to generate a control signal to adjust and calibrate an opening of an inspiratory valve that regulates the driving gas during the medical treatment procedure and a warning signal to indicate that the flow measuring component is not functioning correctly when the flow measuring component malfunctions.

10. The method according to claim 9, wherein each one of the flow measuring component and the flow measuring reference component comprises a flow sensor to detect gas flow rates.

11. The method according to claim 10, wherein the flow measuring component comprises a bidirectional flow sensor, the method further comprises:

detecting a flow direction that one or more fresh gases flows through the bidirectional flow sensor having at least two ports, wherein the one or more fresh gases flow into the bidirectional flow sensor through any of the at least two ports; and
determining a relation between the first flow rate of the gas through the flow measuring reference component and the second flow rate of the gas through the flow measuring component according to the flow direction.

12. The method according to claim 9, further comprising:
removing the container including the one or more gases to be discharged so that the driving gas through the flow measuring reference component flows through the flow measuring reference component at the first flow rate or the third flow rate that is substantially identical to the second flow rate of the one or more gases flowing through the flow measuring component.

13. The method according to claim 10, further comprising:
removing the container including the one or more gases to be discharged so that the driving gas through the flow measuring reference component flows through the flow measuring reference component at the first flow rate or at the third flow rate that is substantially identical to the second flow rate of the one or more gases flowing through the flow measuring component.

14. The method according to claim 11, further comprising:
removing the container including the one or more gases to be discharged so that the driving gas through the flow measuring reference component flows through the flow measuring component at the first flow rate or the third flow rate that is substantially identical to the second flow rate of the one or more gases flowing through the flow measuring component.

15. The method of claim 9, in which the one or more gases to the patient comprises at least one constituent that is not a part of the driving gas flowing through the flow measuring reference component.

16. The method of claim 9, further comprising:
removing the container from the respirator prior to the act of determining the one or more respiration parameters.

17. The method of claim 9, in which the flow measuring reference component does not communicate with a breathing circuit when the breathing circuit is used to deliver the one or more gases to the patient or to extract one or more exhaled gases from a patient.

* * * * *